US011980680B2

(12) United States Patent
Sergheraert

(10) Patent No.: US 11,980,680 B2
(45) Date of Patent: May 14, 2024

(54) KERATIN HYDROLYSATE FOR ORAL COSMETIC USE

(71) Applicant: BRETAGNE CHIMIE FINE, Pleucadeuc (FR)

(72) Inventor: Renaud Sergheraert, Baden (FR)

(73) Assignee: BRETAGNE CHIMIE FINE, Pleucadeuc (FR)

( * ) Notice: Subject to any disclaimer, the term of this patent is extended or adjusted under 35 U.S.C. 154(b) by 16 days.

(21) Appl. No.: 16/643,045

(22) PCT Filed: Aug. 30, 2018

(86) PCT No.: PCT/EP2018/073406
§ 371 (c)(1),
(2) Date: Feb. 28, 2020

(87) PCT Pub. No.: WO2019/043128
PCT Pub. Date: Mar. 7, 2019

(65) Prior Publication Data
US 2020/0206119 A1 Jul. 2, 2020
US 2021/0228466 A9 Jul. 29, 2021

(30) Foreign Application Priority Data

Sep. 1, 2017 (FR) ..................................... 1770921

(51) Int. Cl.
*A61K 8/65* (2006.01)
*A61K 8/44* (2006.01)
*A61K 8/67* (2006.01)
*A61Q 5/00* (2006.01)
*C07K 1/12* (2006.01)
*C07K 14/47* (2006.01)

(52) U.S. Cl.
CPC ................ *A61K 8/65* (2013.01); *A61K 8/447* (2013.01); *A61K 8/675* (2013.01); *A61Q 5/00* (2013.01); *C07K 1/122* (2013.01); *C07K 14/4741* (2013.01)

(58) Field of Classification Search
None
See application file for complete search history.

(56) References Cited

U.S. PATENT DOCUMENTS

| | | | |
|---|---|---|---|
| 1,608,686 A | 11/1926 | Arthur | |
| 4,245,117 A * | 1/1981 | Scherberich | C07C 227/40 562/554 |
| 4,874,893 A | 10/1989 | Flork | |
| 5,698,724 A * | 12/1997 | Anderson | C07F 15/065 556/148 |
| 11,678,680 B2 * | 6/2023 | Duperray | A23J 1/10 426/657 |
| 2013/0209611 A1 * | 8/2013 | Xia | A23J 3/341 426/59 |
| 2020/0206119 A1 * | 7/2020 | Sergheraert | A61K 8/44 |

FOREIGN PATENT DOCUMENTS

| | | |
|---|---|---|
| DE | 244 760 A1 | 4/1987 |
| FR | 2546724 B1 | 5/1989 |
| FR | 2704394 A1 | 11/1994 |
| WO | 2007/083402 A1 * | 7/2007 |
| WO | 2015/014859 A2 | 2/2015 |

OTHER PUBLICATIONS

Emil Abderhalden et al: "Hydrolyse des Keratins aus Horn und aus Wolle", Hoppe-Seyler's Zeitschrift Fuer Physiologische Chemie., vol. 52, No. 3-4, Jan. 1, 1907 (Jan. 1, 1907), pp. 348-367, XP055471234, DE ISSN: 0018-4888 , DOI: 10.1515/ bchm2.1907.52.3-4.348.*
International Search Report with English translation and Written Opinion with Machine translation dated Nov. 15, 2018 in corresponding International Application No. PCT/EP2018/073406; 20 pages.
Barba, C. et al., "Effect of wool keratin proteins and peptides on hair water sorption kinetics", Journal of Thermal Analysis and Calorimetry, Kluwer Academic Publishers, Dordrecht, NL, vol. 102, No. 1, Jan. 30, 2010, pp. 43-48.
Abderhalden, Emil et al., "Hydrolyse des Keratins aus Horn und aus Wolle", Hoppe-Seyler's Zeitschrift Fuer Physiologische Chemie., vol. 52, No. 3-4, Jan. 1, 1907, pp. 348-367.
"New hand, nail care ingredient aids against drying effect of detergents", Focus On Surfactants, Elsevier, Amsterdam, NL, vol. 2005, No. 10, Oct. 1, 2005, p. 4.
Notification of an opposition issued Dec. 8, 2022, in corresponding to European Application No. 18762295.6; 24 pages.
Commission Regulation (EC), No. 152/2009, "Laying down the methods of sampling and analysis for the official control of feed" (Text with EEA relevance), Official Journal of European Union, Jan. 27, 2009, 32009R0152, 130 pages.
Kera Diet, "Keratin Food Grade in Powder", BCF Life Sciences, Traced & Innovative Amino Acids, Nutraceutical, Version 1, www.bcf-lifesciences.com, cited in Notification of opposition issued Dec. 8, 2022, 1 page.

(Continued)

Primary Examiner — Maury A Audet
(74) Attorney, Agent, or Firm — Maier & Maier, PLLC

(57) ABSTRACT

A keratin hydrolysate including at least 88% by weight of free amino acids relative to the total weight of the amino acids of the hydrolysate, the remainder of the hydrolysate being peptides having a molecular mass of less than or equal to 800 Dalton, the hydrolysate also including L-cystine in a content ranging from 4% to 6%, cysteine in a content of less than or equal to 0.1%, and tyrosine in a content of less than or equal to 0.6% by weight, relative to the total weight of the hydrolysate. Also, a process for preparing the hydrolysate, the oral cosmetic use of the hydrolysate for improving the appearance of the nails and/or of the hair, and a dietary supplement including the hydrolysate and optionally vitamins, zinc and/or L-cystine.

17 Claims, No Drawings

(56) References Cited

OTHER PUBLICATIONS

Kera Diet, "Hydrolystate of natural keratin", BCF Life Sciences, Traced & Innovative Amino Acids, Food Supplements, Version 4, 2018, 1 page.

Products and Innovations, BCF Life Sciences, https://web.archive.org/web/20170815005550/http:/www.bcf-lifesciences.com/en/fabrication-2/products-and-innovations/, Aug. 15, 2017, 5 pages.

Exhibitors & Visitors List, Bretagne Commerce International, Vita Foods-Geneva, May 2016 and 2017, 48 pages.

Beer et al., "A Clinical Trial to Investigate the Effect of Cynatine HNS on Hair and Nail Parameters", Hindawi Publishing Corporation, The Scientific World Journal, vol. 2014, Oct. 16, 2014, Article ID 641723, DOI: 10.1155/2014/641723, 7 pages.

List of Category 3 processing plants, Article 24(1)(a) of Regulation (EC) No. 1069/2009, French Ministry of Agriculture, Apr. 25, 2017, 5 pages.

News Article, La Vie de Vos Entreprises, BCF Life Sciences, https://economie.lesinfosdupaysgallo.com/2015/07/02/pleucadeuc-bcf-life-science-lenterprise-modele/, Jul. 2, 2015, 11 pages.

"Analysis and evolution of waste recycling from dawn and feathers processes in France. Final report", Agence de L'Environnement et de la maîtrise de l'énergie (ADEME), Feb. 2003, 63 pages.

Amino EZ, "Mix of Free Amino Acids", BCF Life Sciences, Traced & Innovative Amino Acids, Sport Nutrition, Version 1, Mar. 2016, www.bcf-lifesciences.com, 1 page.

Amino EZ, Nutrition Sportive, "Applications of BCF Life Sciences Products", https://web.archive.org/web/20170323091406/http:www.bcf-lifesciences.com/fr/applications/nutrition-sportive/, 7 pages.

\* cited by examiner

KERATIN HYDROLYSATE FOR ORAL COSMETIC USE

FIELD

The present invention relates to the field of keratin hydrolysates and more particularly to the cosmetic use, orally, of a keratin hydrolysate as agent for improving the quality and appearance of the nails and/or of the hair. It also relates to a dietary supplement comprising this keratin hydrolysate.

BACKGROUND

Hair and nails are part of the family of integuments which are elements that protect the skin from the outside environment. The appearance of the integuments, and notably of the hair, is among the main criteria commonly linked to beauty.

In order to obtain and preserve a quality head of hair, many compositions intended to be applied to the hair such as shampoos, conditioners, balms and oils have been developed.

Dietary supplements also exist that are based on B vitamin(s) and/or sulfur-containing amino acids and that are dedicated to improving the quality of the integuments, notably keratin-based dietary supplements are offered for sale. These keratin-based dietary supplements are described as comprising the 17 main essential amino acids including cysteine in a significant amount.

There still remains a need to provide effective products for improving the quality of the integuments.

The present invention aims to meet this need.

Thus, the inventors have used a keratin hydrolysate, the particular composition of which enables an advantageous improvement in the appearance of the integuments, notably the beauty, quality and strength of the hair and nails, and more particularly an improvement in the brilliance, anchoring, volume, density and gloss of the hair.

Other aspects, advantages and properties of the present invention are presented in the description and examples that follow.

SUMMARY

One subject of the present invention is therefore a keratin hydrolysate having the following features:
- said hydrolysate comprises at least 88% by weight of free amino acids relative to the total weight of the amino acids of the hydrolysate, the remainder of the amino acids of the hydrolysate being in the form of peptides having a molecular mass less than or equal to 800 Dalton,
- said hydrolysate comprises L-cystine in a content ranging from 4% to 6% by weight relative to the total weight of the hydrolysate,
- said hydrolysate comprises cysteine in a content less than or equal to 0.1% by weight relative to the total weight of the hydrolysate,
- said hydrolysate comprises tyrosine in a content less than or equal to 0.6% by weight relative to the total weight of the hydrolysate.

The inventors have shown that, surprisingly, this hydrolysate makes it possible to impart particularly advantageous properties to the integuments. The keratin hydrolysate according to the invention makes it possible to obtain shinier hair that is better anchored at the hair papilla, the head of hair appears to have greater volume.

The nails also appear shinier.

The present invention also targets a method for preparing the keratin hydrolysate according to the invention from a poultry keratin raw material, said method comprising at least the following steps, in this order:
- subjecting the raw material to at least one chemical hydrolysis by means of an acid under conditions suitable for obtaining a hydrolysate comprising at least 88% by weight of free amino acids relative to the total weight of the amino acids of the hydrolysate, the remainder of the amino acids of the hydrolysate being in the form of peptides having a molecular mass less than or equal to 800 Dalton,
- extracting the tyrosine from said hydrolysate,
- optionally drying.

According to a third subject, the invention targets the cosmetic use, orally, of the keratin hydrolysate according to the invention as an agent for improving the quality and/or the appearance of the nails and/or of the hair, notably for improving the anchoring, the gloss and/or the volume and/or the density of the hair.

A fourth subject of the invention targets a dietary supplement, notably intended for improving the appearance of the nails and/or of the hair, comprising a keratin hydrolysate according to the invention or obtained according to the preparation method according to the invention, the dietary supplement comprises from 40% to 60% by weight of keratin hydrolysate relative to the total weight of said dietary supplement.

According to a fifth subject, the invention targets a cosmetic treatment method for improving the quality and/or the appearance of the nails and/or of the hair, notably for improving the quality of the hair, comprising the oral administration, to an individual, of a hydrolysate according to the present invention or of a dietary supplement according to the present invention.

Other subjects, aspects, advantages and properties of the present invention are presented in the description and examples that follow.

DETAILED DESCRIPTION

Hydrolysate

As already mentioned, one of the main features of the keratin hydrolysate according to the present invention is that it has very low contents of two amino acids: tyrosine and cysteine.

Tyrosine is thus present in the keratin hydrolysate according to the present invention in a content less than or equal to 0.6% by weight, preferably less than or equal to 0.5% by weight and preferably less than or equal to 0.4% by weight relative to the total weight of the hydrolysate. This low content of tyrosine is the consequence of the use of a tyrosine extraction step in the method for preparing the hydrolysate.

Advantageously, the hydrolysate does not contain tyrosine, the only traces of this amino acid being due to the limits of the operating conditions, of the equipment used during the extraction step.

Cysteine is present in the keratin hydrolysate according to the present invention in a content less than or equal to 0.1%, preferably less than or equal to 0.05% by weight relative to the total weight of the hydrolysate, more preferably the hydrolysate does not contain cysteine.

On the other hand, the hydrolysate according to the present invention comprises L-cystine, which is a dimer of cysteine, in a significant content. Specifically, the content of L-cystine ranges from 4% to 6% by weight, preferably from 4.5% to 5.5% by weight relative to the total weight of the hydrolysate.

The hydrolysate according to the present invention comprises at least 88%, preferably at least 93% and more preferably at least 95% by weight of free amino acids relative to the total weight of the amino acids of the hydrolysate, the remainder of the amino acids of the hydrolysate being in the form of peptides having a molecular mass less than or equal to 800 Dalton.

Specifically, the hydrolysate essentially comprises amino acids: free amino acids (at least 88% by weight relative to the total weight of the amino acids) and amino acids bound to form peptides, the hydrolysate further comprising mineral material and water.

Advantageously, the content of total (free and bound) amino acids of the hydrolysate ranges from 80% to 90% by weight relative to the total weight of the hydrolysate.

According to a first preferred embodiment, the keratin hydrolysate according to the invention has the following composition of total amino acids: a glycine content ranging from 7% to 10% by weight; an alanine content ranging from 4% to 6% by weight; a valine content ranging from 6% to 10% by weight; a proline content ranging from 9% to 14% by weight.

According to a second preferred embodiment, the keratin hydrolysate according to the invention comprises the following composition of total amino acids: an aspartic acid content ranging from 6% to 9% by weight, preferably 7.6% by weight; a threonine content ranging from 4% to 6% by weight, preferably 5.1% by weight; a serine content ranging from 10% to 15% by weight, preferably 12.4% by weight; a glutamic acid content ranging from 9% to 14% by weight, preferably 11.4% by weight; a glycine content ranging from 7% to 10% by weight, preferably 8.6% by weight; an alanine content ranging from 4% to 6% by weight, preferably 5.0% by weight; a valine content ranging from 6% to 10% by weight, preferably 8.2% by weight; a methionine content ranging from 0.1% to 0.4% by weight, preferably 0.2% by weight; an isoleucine content ranging from 4% to 6% by weight, preferably 4.6% by weight; a leucine content ranging from 6% to 9% by weight, preferably 7.7% by weight; a tyrosine content ranging from 0.1% to 0.5% by weight, preferably 0.3% by weight; a phenylalanine content ranging from 2% to 3% by weight, preferably 2.5% by weight; a lysine content ranging from 1% to 3% by weight, preferably 2.0% by weight, a histidine content ranging from 0.4% to 1% by weight, preferably 0.7% by weight; an arginine content ranging from 5% to 8% by weight, preferably 6.4% by weight; a proline content ranging from 9% to 14% by weight, preferably 11.8% by weight, a tryptophan content of less than 0.1%, preferably 0% by weight and an L-cystine content ranging from 4% to 6% by weight, preferably 5.5% by weight.

According to a third preferred embodiment, the keratin hydrolysate according to the invention comprises the following composition of total amino acids: an aspartic acid content ranging from 6% to 9% by weight, a threonine content ranging from 4% to 6% by weight; a serine content ranging from 10% to 15% by weight; a glutamic acid content ranging from 9% to 14% by weight; a glycine content ranging from 7% to 10% by weight; an alanine content ranging from 4% to 6% by weight; a valine content ranging from 6% to 10% by weight; a methionine content of 0.2% by weight; an isoleucine content ranging from 4% to 6% by weight; a leucine content ranging from 6% to 9% by weight; a tyrosine content ranging from 0.1% to 0.5% by weight; a phenylalanine content ranging from 2% to 3% by weight; a lysine content ranging from 1 to 3% by weight, a histidine content ranging from 0.4% to 1% by weight; an arginine content ranging from 5% to 8% by weight; a proline content ranging from 9% to 14% by weight and an L-cystine content ranging from 4% to 6% by weight.

Advantageously, the content of mineral material of said hydrolysate is less than or equal to 9% by weight, preferably less than 8% by weight relative to the total weight of the hydrolysate.

The content of mineral material is determined after calcining the hydrolysate at 550° C. for 4 hours.

The amino acids are assayed according to a method adapted from the EC 152/2009 regulation.

According to this method, for the determination of the amounts of total amino acids, a hydrolysis using an acid is carried out beforehand.

For the determination of the amounts of free and total amino acids, amino acids are separated by chromatography (HPLC) with an ion-exchange column and assayed by reaction with ninhydrin and photometric detection generally at 570 nm.

Without wishing to be tied to any one theory, it appears that carrying out a thorough chemical hydrolysis that makes it possible to lead to these characteristics, notably a molecular mass of the peptides present of less than or equal to 800 Dalton, imparts particular properties to the hydrolysate.

Another advantage of the hydrolysate according to the present invention is that it is very digestible, moreover it is known to be of food grade. The hydrolysate according to the invention has a true digestibility of the amino acids of at least 90%. This value is very close to the maximum possible (100%).

The digestibility is measured in vivo according to the method described by Cozannet P., Primot Y., Gady C., Métayer J. P., Lessire M., Skiba F., Noblet J. in "Standardised amino acid digestibility of wheat distillers' dried grains with solubles in force-fed cockerels", British Poultry Science, February 2011; 52(1):72-81.

More particularly the keratin hydrolysate according to the present invention comprises L-cystine and 16 amino acids distributed in accordance with the profile of total amino acids presented in table 1: in the first column, the preferred ranges of each of the constituents are presented, and in the second column the preferred contents for each of the constituents are presented.

TABLE 1

| Amino acid/ peptide | Content range in the hydrolysate (wt%) | Preferred content in the hydrolysate (wt%) |
|---|---|---|
| Asp | 6-9 | 7.6 |
| Thr | 4-6 | 5.1 |
| Ser | 10-15 | 12.4 |
| Glu | 9-14 | 11.4 |
| Gly | 7-10 | 8.6 |
| Ala | 4-6 | 5.0 |
| Val | 6-10 | 8.2 |
| Met | 0.1-0.4 | 0.2 |
| L-Cystine | 4-6 | 5.5 |

TABLE 1-continued

| Amino acid/ peptide | Content range in the hydrolysate (wt%) | Preferred content in the hydrolysate (wt%) |
|---|---|---|
| Ile | 4-6 | 4.6 |
| Leu | 6-9 | 7.7 |
| Tyr | 0.1-0.5 | 0.3 |
| Phe | 2-3 | 2.5 |
| Lys | 1-3 | 2.0 |
| His | 0.4-1 | 0.7 |
| Arg | 5-8 | 6.4 |
| Pro | 9-14 | 11.8 |
| total | | 100 |

Unlike certain keratin hydrolysates, the hydrolysate according to the present invention does not contain sulfoxycysteine.

Hydrolysate Preparation Method

As already mentioned, the present invention also relates to a method for preparing the keratin hydrolysate from natural, notably poultry, keratin materials, advantageously from poultry feathers.

This natural keratin material predominantly comprises polypeptides of high molecular weight and having the highly branched structure that makes it not very accessible to enzymes and which mean that said natural keratin material is not digestible.

Advantageously, said hydrolysate is a hydrolysate of poultry keratin raw material.

As poultry, mention may be made of hens, chickens, turkeys, ducks, etc.

In particular, the hydrolysate according to the present invention is not obtained from human keratin such as the hair.

The method for preparing the keratin hydrolysate according to the invention uses at least one chemical hydrolysis by means of an acid under conditions suitable for obtaining a hydrolysate comprising at least 88% by weight of free amino acids relative to the total weight of the amino acids of the hydrolysate, the remainder of the amino acids of the hydrolysate being in the form of peptides having a molecular mass less than or equal to 800 Dalton.

The percentage of peptides in the hydrolysate according to the invention generally ranges from 5% to 12% by weight relative to the total weight of the hydrolysate.

Specifically, since the hydrolysis is partial, the percentage of peptides in the hydrolysate is not zero, preferably it is at least 5% by weight.

The chemical hydrolysis of the raw material is carried out by means of an acid, preferably a strong acid selected from hydrochloric, phosphoric and sulfuric acids, preferably hydrochloric acid.

The chemical hydrolysis is generally carried out for a time ranging from 1 hour to 8 hours, preferably ranging from 6 to 7 hours at a temperature ranging from 110° C. to 115° C.

According to a particular variant, the chemical hydrolysis is carried out in two steps:
- a first chemical hydrolysis carried out at a temperature ranging from 60° C. to 80° C. for a period ranging from 4 to 5 hours, then
- a second chemical hydrolysis carried out at a temperature ranging from 100° C. to 115° C. for a period ranging from 5 to 7 hours, it being possible for the two hydrolyses to be carried out without an intermediate waiting step or by staging an intermediate waiting step of between 1 hour and 7 days.

More specifically, the first chemical hydrolysis is carried out at 72° C. for 4.5 hours and the second chemical hydrolysis is carried out at 107° C. for 6 hours, a waiting time of 24 to 80 hours being staged between the two chemical hydrolyses.

The step of extracting tyrosine is carried out by means of a base preferably selected from sodium hydroxide or potassium hydroxide, preferably sodium hydroxide.

The step of extracting tyrosine is a conventional step, the implementation of which falls within the competence of a person skilled in the art.

The steps of chemical hydrolysis and of extracting tyrosine may be followed by optional steps of purifying the hydrolysate obtained.

The steps of chemical hydrolysis and of extracting tyrosine may be followed by optional steps of concentrating the hydrolysate obtained.

The steps of chemical hydrolysis and of extracting tyrosine may be followed by optional steps of drying, for example by spraying.

The purifying, concentrating and drying steps are conventional steps, the implementation of which fall within the competence of a person skilled in the art.

Advantageously, the keratin hydrolysate obtained is spray-dried in order to obtain the hydrolysate in solid form.

The keratin hydrolysate obtained is soluble in water, specifically 1 g of keratin hydrolysate according to the invention is soluble in 5 ml of water.

Uses

As already mentioned, the present invention targets the cosmetic use, orally, of the keratin hydrolysate according to the invention or obtained according to the preparation method according to the invention as an agent for improving the quality and/or the appearance of the nails and/or of the hair, notably for improving the anchoring, the gloss and/or the volume and/or the density of the hair.

Dietary Supplement

The dietary supplement according to the present invention is a cosmetic composition intended for oral administration, it may also be described as a "nutraceutical composition". Said dietary supplement does not belong to the therapeutic field.

The dietary supplement according to the present invention comprises at least 28% by weight of free amino acids, advantageously between 28% and 47.5% by weight of free amino acids relative to the total weight of said dietary supplement.

Advantageously, the dietary supplement according to the present invention comprises no free amino acids other than those contained in the hydrolysate with the exception of L-cystine which may be added in the form of additional L-cystine.

The dietary supplement according to the present invention generally comprises an amount by weight of additional L-cystine equal to the amount by weight of the hydrolysate.

Preferably, the dietary supplement comprises a keratin hydrolysate according to the invention in a content ranging from 0.001 to 2 g, preferably from 0.5 to 1.5 g and preferably around 0.8 to 1.2 g.

Besides the keratin hydrolysate according to the present invention, the dietary supplement according to the present invention also comprises at least one component selected from the group consisting of zinc or a salt thereof, copper or a salt thereof, B vitamins, notably vitamin B3, B5, B6 and/or B8, and the mixtures of these components.

As B vitamins that can be used in the dietary supplement according to the present invention, mention may be made of the vitamins B3, B5, B6 and B8 and also the derivatives thereof, and the mixtures of vitamins and derivatives.

Preferably, the dietary supplement according to the present invention comprises zinc or a salt thereof, copper or a salt thereof, and vitamins B3, B5, B6 and B8.

The vitamin B3 content of the dietary supplement according to the present invention ranges from 1 to 20 mg, preferably from 5 to 15 mg.

Vitamin B3 (or vitamin PP) may be present in the dietary supplement in the form of one or more compounds such as nicotinamide (or niacinamide), nicotinic acid (or niacin), nicotinyl alcohol, and also the salts and derivatives thereof.

As derivatives, mention may be made of the esters of nicotinic acid such as, for example, tocopheryl nicotinate, nicotinic amino acids, carboxylic acid esters of nicotinyl alcohol, nicotinic acid N-oxide and niacinamide N-oxide.

As salts, any suitably innocuous salt is understood.

Preferably, nicotinamide is used in the dietary supplement according to the invention.

The dietary supplement according to the present invention allows a daily administration of vitamin B3 ranging from 0.00001 g to 1 g, preferably from 0.0001 g to 0.5 g and preferably from 0.0005 g to 0.1 g.

Advantageously, the dietary supplement is formulated so as to allow a daily administration of vitamin B3 corresponding to a content ranging from 15 to 20 mg of nicotinamide.

Advantageously the content of vitamin B3 in the dietary supplement corresponds to the maximum content authorized by the current regulations.

Vitamin B5 corresponds to pantothenic acid. It may be present in the dietary supplement in the pantothenic acid form or in the form of a salt of this acid.

As salts, any suitably innocuous salt is understood, in particular calcium pantothenate.

Preferably, calcium pantothenate is used in the dietary supplement according to the invention.

The dietary supplement according to the present invention allows a daily administration of vitamin B5 ranging from 0.00001 g to 1 g, preferably from 0.0001 g to 0.5 g and preferably from 0.0005 g to 0.1 g.

Advantageously, the dietary supplement is formulated so as to allow a daily administration of vitamin B5 corresponding to a content ranging from 10 to 15 mg of calcium pantothenate.

Advantageously the content of vitamin B5 in the dietary supplement corresponds to the maximum content authorized by the current regulations.

Vitamin B6 may be present in the dietary supplement in the form of one or more compounds such as pyridoxine, pyridoxic acid, pyridoxine esters such as pyridoxine tripalmitate, pyridoxine amines such as pyridoxamine, and also the salts and derivatives thereof.

As salts, any suitably innocuous salt is understood, in particular pyridoxine hydrochloride.

As derivatives, mention may be made of the compounds selected from the group consisting of pyridoxal, pyridoxal phosphate.

Preferably, pyridoxine hydrochloride is used in the dietary supplement according to the invention.

The dietary supplement according to the present invention allows a daily administration of vitamin B6 ranging from 0.00001 g to 1 g, preferably from 0.0001 g to 0.5 g and preferably from 0.0005 g to 0.1 g.

Advantageously, the dietary supplement is formulated so as to allow a daily administration of vitamin B6 corresponding to a content ranging from 0.1 to 0.6 mg of pyridoxine hydrochloride.

Advantageously the content of vitamin B6 in the dietary supplement corresponds to the maximum content authorized by the current regulations.

The dietary supplement according to the present invention allows a daily administration of vitamin B8 ranging from 0.00001 g to 1 g, preferably from 0.0001 g to 0.5 g and preferably from 0.0005 g to 0.1 g.

Advantageously, the dietary supplement is formulated so as to allow a daily administration of vitamin B8 ranging from 0.4 to 0.6 mg.

Advantageously the content of vitamin B8 in the dietary supplement corresponds to the maximum content authorized by the current regulations.

Of course, the salts used in the formulation of the dietary supplement are chosen for their innocuousness. Mention may notably be made of zinc sulfate and copper sulfate and also the chelated forms thereof.

Advantageously, the dietary supplement is formulated so as to allow a daily administration of zinc ranging from 8 to 12 mg.

Advantageously the content of zinc in the dietary supplement corresponds to the maximum content authorized by the current regulations.

Advantageously, the dietary supplement is formulated so as to allow a daily administration of copper ranging from 1 to 2 mg.

Advantageously the content of copper in the dietary supplement corresponds to the maximum content authorized by the current regulations.

Advantageously, the dietary supplement comprises, besides the L-cystine contained in the hydrolysate, additional L-cystine, preferably the amount by weight of the additional L-cystine is equal to the amount by weight of the hydrolysate.

Preferably, the dietary supplement comprises additional L-cystine in a content ranging from 0.001 to 2 g, preferably from 0.5 to 1.5 g and preferably around 0.8 to 1.2 g.

More particularly, the dietary supplement according to the invention comprises:
- a keratin hydrolysate according to the invention or obtained according to the preparation method according to the invention in a content ranging from 0.001 to 2 g, preferably from 0.5 to 1.5 g and preferably around 0.8 to 1.2 g,
- vitamin B3 in a content corresponding to 1% to 3% by weight of nicotinamide relative to the weight of the hydrolysate,
- vitamin B5 in a content corresponding to 1% to 2% by weight of calcium pantothenate relative to the weight of the hydrolysate,
- vitamin B6 in a content corresponding to 0.1% to 0.5% by weight of pyridoxine hydrochloride relative to the weight of the hydrolysate,
- vitamin B8 in a content ranging from 0.01% to 0.1% relative to the weight of the hydrolysate,
- zinc or a salt thereof in a content ranging from 0.5% to 2% of zinc relative to the weight of the hydrolysate,
- copper or a salt thereof in a content ranging from 0.05% to 0.5% of copper relative to the weight of the hydrolysate,
- and optionally, additional L-cystine in an amount by weight equal to the amount by weight of the hydrolysate.

The dietary supplement in accordance with the invention further comprises a physiologically acceptable carrier, in accordance with oral use.

The dietary supplement in accordance with the invention may be formulated with the excipients normally used in compositions intended for oral administration, notably humectants, thickeners, texturing agents, flavoring agents, coating agents, preservatives, antioxidants, colourants, plant extracts such as for example a horsetail extract.

Of course, a person skilled in the art will take care to select these excipients so as not to impair the properties of the dietary supplement.

The dietary supplement in accordance with the invention may be formulated in one of the following presentation forms: a gel capsule, a sugar-coated tablet, a tablet, a soft or hard capsule, or else a suspension, a solution, a gel.

The formulation of the dietary supplement in accordance with the invention implements conventional methods which fall within the general competence of a person skilled in the art.

Oral Cosmetic Treatment Method

The present invention further relates to a cosmetic method for improving the quality and/or the appearance of the nails and/or of the hair, notably for improving the quality of the hair comprising the oral administration, to an individual, of a hydrolysate according to the present invention or of a dietary supplement according to the present invention as defined above.

Thus, the method according to the present invention is a cosmetic method insofar as it makes it possible to improve the condition and the esthetic nature of the nails and/or of the hair. The hydrolysate according to the present invention and the dietary supplement according to the present invention may be used for several months without medical prescription which clearly places them outside of the therapeutic field.

Advantageously, the method according to the present invention makes it possible to administer the following daily doses to an individual:
- a keratin hydrolysate according to the invention in a content ranging from 0.001 to 2 g, preferably from 0.5 to 1.5 g and preferably around 0.8 to 1.2 g;
- vitamin B3 in a content corresponding to a content ranging from 0.015 to 0.020 g of nicotinamide;
- vitamin B5 in a content corresponding to a content ranging from 0.010 to 0.015 g of calcium pantothenate;
- vitamin B6 in a content corresponding to a content ranging from 0.0004 to 0.0006 g of pyridoxine hydrochloride;
- vitamin B8 in a content ranging from 0.0004 to 0.0006 g;
- zinc or a salt thereof in a zinc content ranging from 0.008 to 0.0012 g;
- copper or a salt thereof in a copper content ranging from 0.001 to 0.002 g;
- optionally additional L-cystine in an amount by weight equal to the amount by weight of the hydrolysate.

The method according to the invention is generally implemented by a daily administration of the hydrolysate according to the present invention or of the dietary supplement according to the present invention. This administration may be carried out as a single daily dose, as two daily doses, as three daily doses or even four daily doses, for example at mealtimes.

The method according to the invention is generally implemented over a period varying from one to several weeks or even several months. It being possible for this treatment period to be repeated several times in the course of a year.

The following examples aim to illustrate the invention without limiting the scope thereof.

EXAMPLES

Example 1—Hydrolysates

Preparation of Hydrolysate I 4500 kg of poultry feathers are introduced into a 15 000 liter reactor/hydrolyzer.

A first step of chemical hydrolysis is carried out by adding 18 000 liters of hydrochloric acid (24%), the hydrolysis is carried out at 72° C. for 4.5 hours.

The product obtained is stored for 48 hours at ambient temperature (intermediate waiting step).

Next, a second chemical hydrolysis is carried out by heating at 107° C. for 6 hours without addition of acid.

The product obtained is left to cool.

Next, a step of extracting tyrosine is carried out by raising the pH to around 7 using sodium hydroxide.

The solution obtained is spray-dried.

4200 kg of hydrolysate in dry form are obtained.

Hydrolysate II

By way of comparison, use is made of hydrolysate II which is a hydrolysate derived from sheep's wool, the composition of which is presented in table 2.

Determination of the Composition of the Hydrolysates

The amino acids are assayed according to a method adapted from EC regulation 152/2009.

The amino acids are separated by chromatography (HPLC) with an ion-exchange column and assayed by reaction with ninhydrin and photometric detection at 570 nm.

TABLE 2

| Amino acid/peptide | Content in hydrolysate I (wt%) | Content in hydrolysate II (wt%) |
|---|---|---|
| Asp | 7.6 | 7.8 |
| Thr | 5.1 | 6.5 |
| Ser | 12.4 | 9.3 |
| Glu | 11.4 | 15.8 |
| Gly | 8.6 | 4.8 |
| Ala | 5.0 | 4.5 |
| Val | 8.2 | 6.1 |
| Met | 0.2 | 0.5 |
| L-Cystine | 5.5 | 7.1 |
| Ile | 4.6 | 3.8 |
| Leu | 7.7 | 8.9 |
| Tyr | 0.3 | 3.1 |
| Phe | 2.5 | 3.2 |
| Lys | 2.0 | 2.7 |
| His | 0.7 | 0.8 |
| Arg | 6.4 | 9.2 |
| Pro | 11.8 | 5.9 |
| total | 100 | 100 |

Hydrolysate I comprises 6.6% by weight of mineral materials and hydrolysate II comprises 29.6% by weight of mineral material.

Hydrolysate I comprises 83.3% by weight of free amino acids, hydrolysate II comprises less than 2% by weight of free amino acids relative to the total weight of the hydrolysate.

Example 2—Digestibility

Presented in table 3 are the true digestibility coefficients of each of the amino acids of hydrolysates I and II, expressed as a percentage, and also the mean value of true digestibility of the total of the amino acids.

These values were obtained according to the following protocol on cecectomized roosters, which is a reference model for measurement of the bioavailability of amino acids in the animal kingdom.

Experimental Protocol

The digestibility measurements are carried out on cecectomized adult roosters housed in individual cages and fed outside of the test period with a standard diet.

For each hydrolysate, 2 repetitions of 4 cecectomized roosters are used.

All the animals are taken off feed for 24 h before ingesting a single 80 g meal composed of 24 g of sample (hydrolysate I or II) mixed with 56 g of sugar.

All the feces (=fecal matter), including the endogenous losses, are collected over the following 48 h in two periods of 24 h to prevent the possible fermentation and deterioration thereof.

These feces, excluding all contaminations such as feathers for example, are carefully removed before being frozen (−80° C.).

The feces are then dried in an oven, grouped together and mixed into 2 pools corresponding to the 2 repetitions of 4 animals used for each of the 2 hydrolysates.

For each hydrolysate, the 2 pools are analyzed.

Nutritional analyses (solids content, crude proteins (Dumas method) and amino acids) are carried out on the hydrolysates, the rooster feces and also on the endogenous losses.

This data is used to calculate the true digestibility of the proteins and of the amino acids.

For the digestibility of the proteins, owing to the contamination of the excreta of birds by uric nitrogen, the protein nitrogen is measured in the feces (Terpstra method).

The true digestibility of the nutrients measured as a percentage is therefore calculated according to a quantitative method by the difference between the amount of hydrolysate ingested and the amount of feces excreted, corrected for the endogenous losses according to the following formulae:

$$\text{True digestibility of proteins \%} = \frac{\text{hydrolysate ingested proteins} - (\text{feces excreted proteins} - \text{endogenous excreted proteins})}{\text{hydrolysate ingested proteins}} \times 100$$

$$\text{True digestibility of amino A. \%} = \frac{\text{hydrolysate ingested amino acid} - (\text{feces excreted amino acid} - \text{endogenous excreted amino acid})}{\text{hydrolysate ingested amino acid}} \times 100$$

The digestibility values of the hydrolysates I and II appear in table 3 below:

TABLE 3

| Amino acid/peptide (AA) | True digestibility coefficient of the AA of hydrolysate I (%) | True digestibility coefficient of the AA of hydrolysate II (%) |
| --- | --- | --- |
| Asp | 97.55 | 73.88 |
| Thr | 95.70 | 72.64 |
| Ser | 98.91 | 75.72 |
| Glu | 94.27 | 76.03 |
| Gly | 91.69 | 52.52 |
| Ala | 97.46 | 77.24 |
| Val | 98.04 | 76.85 |
| Met | 96.05 | 76.35 |
| L-Cystine | 84.39 | 69.26 |
| Ile | 98.28 | 78.61 |
| Leu | 98.64 | 84.24 |
| Tyr | 99.19 | 82.59 |
| Phe | 99.17 | 81.70 |
| Lys | 97.91 | 75.44 |
| His | 93.40 | 70.21 |
| Arg | 96.25 | 78.74 |
| Pro | 98.66 | 66.85 |
| Total | 96.21 | 74.64 |

The true digestibility of the amino acids of hydrolysate I according to the invention is very high since it is very close to the maximum possible (100%) and it is much greater than that of the amino acids of the comparative hydrolysate II.

The hydrolysate according to the invention is consequently much more digestible by the organism than the comparative hydrolysate, as shown by its mean true digestibility of the amino acids which is 21.57 points higher than that of the comparative hydrolysate.

Example 3—Dietary Supplement

Preparation of the Dietary Supplement

Table 4—Dietary Supplement in Gel Capsule Form

The following ingredients are weighed, mixed at ambient temperature and made into gel capsules.

The amounts are indicated in mg

| Ingredients | Formula A Composition according to the invention | Formula B Composition according to the invention | Formula C (placebo) |
| --- | --- | --- | --- |
| Maltodextrin | 250 | 0 | 500 |
| Keratin hydrolysate I | 250 | 250 | 0 |
| Keratin hydrolysate II | 0 | 0 | 0 |
| L-Cystine | 0 | 250 | 0 |
| Magnesium stearate | 14 | 14 | 14 |
| Zinc sulfate (22% Zn) | 11.36 | 11.36 | 0 |
| Silica | 5 | 5 | 5 |
| Vitamin B3 (nicotinamide) 99% a.m. | 4.5 | 4.5 | 0 |
| Vitamin B5 (calcium D-pantothenate) 92% a.m. | 3.72 | 3.72 | 0 |
| Solids content of the aerial part of horsetail | 2.5 | 2.5 | 0 |
| Copper sulfate (25% Cu) | 1.48 | 1.48 | 0 |

-continued

| Ingredients | Formula A Composition according to the invention | Formula B Composition according to the invention | Formula C (placebo) |
|---|---|---|---|
| Vitamin B6 (pyridoxine hydrochloride) 83% a.m. | 0.63 | 0.63 | 0 |
| Vitamin B8 (biotin) 99.75% a.m. | 0.15 | 0.15 | 0 |

Study

The dietary supplement was administered in a proportion of 4 gel capsules per day (2 gel capsules in the morning and 2 gel capsules in the evening) for 90 days.

The study was carried out on 60 subjects, double-blind, with random distribution and in the presence of a placebo (20 subjects received Formula A, 20 subjects received Formula B and 20 subjects received the placebo Formula C).

The subjects accepted met the following criteria:

subjects in good health, age from 30 to 60 years old, hair of dark natural color: brown or black, in each group 20% of the subjects had previously carried out a bleaching of the hair, subject having a tendency to lose hair and having brittle nails.

Hair

Regarding the hair, the gloss, the presence of telogen effluvium, the density and the volume were evaluated.

The gloss was measured using a CM 700D spectrophotometer/colorimeter (Konica-Minolta). The parameter measured was the gloss value at 8°.

The presence of telogen effluvium is measured by means of a pull test. The pull test was used to determine the quality of the anchoring of the hair at the hair papilla. Gentle pulling is exerted on the locks of hair (around 60 hairs) in three different zones of the head of hair: frontal zone, occipital zone and temporal zone and the number of hairs removed is counted.

Normally less than three hairs in telogen phase should be pulled out with each pull.

If at least three hairs in telogen phase are pulled out with each pull or if more than 10 hairs in total are pulled out, the pull test is considered positive and reveals the presence of telogen effluvium.

The density measured as number of hairs per $cm^2$ is obtained with a phototrichogram, established according to the recommendations of the Trichoscan® registered reference method.

The volume of the head of hair is determined by a dermatologist by comparing digital photographs taken at t=0, at 45 days and at 90 days. The camera used is a NIKON D300/600 equipped with a macro lens, an independent flash and polarized (crossed or parallel) filters. For each subject, 4 photos are taken: two in the zone of the vertex (one with a crossed polarized filter and one with a parallel polarized filter) and two in the frontal zone (one with a crossed polarized filter and one with a parallel polarized filter).

Each time scores are given, then the number of subjects having an increase in the head of hair is determined.

Nails

Regarding the nails, the gloss and the appearance/quality were evaluated.

The gloss was measured using a CM 700D spectrophotometer/colorimeter (Konica-Minolta). The parameter measured was the gloss value at 8°.

The quality/appearance of the nails is determined, scoring by a dermatologist.

TABLE 5

| Parameter | Formula A Tested at 45 days | Formula A Tested at 90 days | Formula B Tested at 45 days |
|---|---|---|---|
| hair | | | |
| % anagen | 82.3* ± 0.7 (+3.6%) | 87.7* ± 0.6 (+9.1%) | 82.7* ± 0.7 (+4.3%) |
| % telogen | 17.8* ± 0.7 (−3.6%) | 12.3* ± 0.6 (−9.1%) | 17.3* ± 0.7 (−4.3%) |
| Pull test/t0 | 8.9* ± 0.4 (−26.5%) | 8.1* ± 0.4 (−32.7%) | 9.6* ± 0.5 (−24.3%) |
| Gloss/t0 | 3.98* ± 0.45 (+23.8%) | 4.99* ± 0.53 (+57.0%) | 4.08* ± 0.38) (+31.4%) |
| Volume** | 40.0%* | 65.0%* | 40.0%* |
| Density | 194.7 ± 6.7 (+2.1%) | 205.9* ± 6.4 (+13.3%) | 198.9 ± 4.8 (+3.4%) |
| Nails | | | |
| Gloss/t0 | 9.54* ± 0.93 (+33.1%) | 9.57 ± 0.86 (+35.7%) | 9.02* ± 0.92 (+28.5%) |
| Improvement in appearance scored by a dermatologist | 30.0% | 60.0%* | 35.0% |

| Parameter | Formula B Tested at 90 days | Formula C Tested at 45 days | Formula C Tested at 90 days |
|---|---|---|---|
| hair | | | |
| % anagen | 88.2* ± 0.5 (+9.7%) | 78.6 ± 0.7 (−0.4%) | 82.2 ± 0.7 (+3.2%) |
| % telogen | 11.8* ± 0.5 (−9.7%) | 21.4 ± 0.7 (+0.4%) | 17.9 ± 0.7 (−3.2%) |
| Pull test/t0 | 8.3* ± 0.3 (−34.0%) | 12.4 ± 0.5 (+1.0%) | 11.0 ± 0.5 (−10.6%) |
| Gloss/t0 | 4.85* ± 0.43 (+58.9%) | 3.28 ± 0.36 (−1.9%) | 3.53 ± 0.39 (+6.4%) |
| Volume** | 75.0%* | 5.0% | 10.0% |
| Density | 211.3* ± 4.9 (+15.8%) | 194.0 ± 7.1 (+0.2%) | 195.0 ± 7.2 (+1.8%) |
| Nails | | | |
| Gloss/t0 | 10.74* ± 0.99 (+58.4%) | 7.76 ± 0.59 (+6.7%) | 8.45 ± 0.69 (+17.2%) |
| Improvement in appearance scored by a dermatologist | 70.0%* | 15.0% | 20.0% |

*: Significantly different from the placebo formula
( ): between parentheses, percentage increase relative to the start of the test
**: % of subjects having an increase in the volume of their head of hair.

TABLE 6

The growth of the nails is measured from digital photographs using a morphometric image analysis technique. The nails are cut and the growth is measured between D − 7 and D + 7 (measurement t = 0) then between D38 and D52 (measurement t = 45) then between D83 and D102 (measurement t = 90).

| | Form. A Tested at t = 0 | Form. A Tested at 45 days | Form. A Tested at 90 days | Form. B Tested at t = 0 | Form. B Tested at 45 days | Form. B Tested at 90 days | Form. C Tested at t = 0 | Form. C Tested at 45 days | Form. C Tested at 90 days |
|---|---|---|---|---|---|---|---|---|---|
| Nail growth | 1.24 ± 0.07 | 1.31 ± 0.07 | 1.38* ± 0.08 | 1.21 ± 0.05 | 1.30* ± 0.06 | 1.43* ± 0.07 | 1.26 ± 0.06 | 1.28 ± 0.05 | 1.28 ± 0.06 |

*Significantly different from formula C (placebo)

Results

Regarding the Hair

Formula A, in accordance with the invention, enables an improvement in the anchoring of the hair, in the gloss of the hair, in the density and in the volume of the head of hair. The combination of the hydrolysate according to the invention with additional L-cystine, formula B, in accordance with the invention, makes it possible to further improve the results obtained.

Regarding the Nails

Formula A, in accordance with the invention, enables an increase in the gloss, in the quality and in the growth of the nails.

These results show that the administration of the formula A comprising a keratin hydrolysate, vitamins, copper and zinc enables the improvement of the appearance of the hair and of the nails compared to the placebo formula.

Furthermore, the combination of the hydrolysate according to the invention with additional L-cystine makes it possible to further improve the results.

The invention claimed is:

1. A keratin hydrolysate comprising, amino acids and mineral material with contents by weight of the hydrolysate consisting of:
   aspartic acid ranging from 6% to 9%;
   threonine ranging from 4% to 6%;
   serine ranging from 10% to 15%;
   glutamic acid ranging from 9% to 14%;
   glycine ranging from 7% to 10%;
   alanine ranging from 4% to 6%;
   valine ranging from 6% to 10%;
   methionine ranging from 0.1% to 0.4%;
   isoleucine ranging from 4% to 6%;
   leucine ranging from 6% to 9%;
   phenylalanine ranging from 2% to 3%;
   lysine ranging from 1% to 3%;
   histidine ranging from 0.4% to 1%;
   arginine ranging from 5% to 8%;
   proline ranging from 9% to 14%;
   tryptophan of less than 0.1%;
   L-cystine ranging from 4% to 6%;
   cysteine of less than or equal to 0.1%;
   tyrosine ranging from 0.1% to 0.5%; and
   mineral material of less than 8%;
   wherein free amino acids are from 88% to 95% by weight of the total weight of the amino acids of the hydrolysate, the remainder of the amino acids of the hydrolysate being in the form of peptides having a molecular mass less than or equal to 800 Dalton, the peptides being from 5% to 12% by weight relative to the total weight of hydrolysate;
   wherein the keratin hydrolysate is a hydrolysate of poultry feathers selected from the group consisting of chicken feathers, turkey feathers, duck feathers, and mixtures thereof; and
   wherein the keratin hydrolysate is prepared by a method comprising at least the following steps, in this order:
      subjecting the poultry feathers to at least one chemical hydrolysis by means of an acid under conditions suitable for obtaining the keratin hydrolysate comprising from 88% to 95% by weight of free amino acids relative to the total weight of the amino acids of the hydrolysate, the remainder of the amino acids of the hydrolysate being in the form of peptides having a molecular mass less than or equal to 800 Dalton, the peptides being from 5% to 12% by weight relative to the total weight of hydrolysate;
      extracting the tyrosine from said hydrolysate; and
      optionally drying
   wherein the at least one chemical hydrolysis is carried out in two steps:
      a first chemical hydrolysis carried out at a temperature ranging from 60° C. to 80° C. for a period ranging from 4 to 5 hours, then
      a second chemical hydrolysis carried out at a temperature ranging from 100° C. to 115° C. for a period ranging from 5 to 7 hours, and
   wherein the two hydrolyses may be carried out without an intermediate waiting step or by staging an intermediate waiting step of between 1 hour and 7 days.

2. The keratin hydrolysate as claimed in claim 1, wherein the amino acid and mineral contents by weight of the hydrolysate consist of:
   aspartic acid ranging from 6.5% to 7.5%;
   threonine ranging from 4.0% to 4.8%;
   serine ranging from 10.3% to 11.7%;
   glutamic acid ranging from 9.6% to 10.6%;
   glycine ranging from 7.2% to 8.2%;
   alanine ranging from 4.5% to 4.8%;
   valine ranging from 6.9% to 7.5%;
   methionine ranging from 0.1% to 0.2%;
   isoleucine ranging from 4% to 4.7%;
   leucine ranging from 6.0% to 7.0%;
   phenylalanine ranging from 2% to 2.6%;
   lysine ranging from 1.6% to 1.9%;
   histidine ranging from 0.5% to 0.7%;
   arginine ranging from 4.9% to 6.0%;
   proline ranging from 8.6% to 10.3%;
   tryptophan of less than 0.1%;
   L-cystine ranging from 4.7% to 6%;
   cysteine of less than or equal to 0.1%;
   tyrosine ranging from 0.1% to 0.4%; and
   mineral material of less than 8%;
   wherein free amino acids are from 88% to 95% by weight of the total weight of the amino acids of the hydrolysate, the remainder of the amino acids of the hydrolysate being in the form of peptides having a molecular mass less than or equal to 800 Dalton, the peptides being from 5% to 12% by weight relative to the total weight of hydrolysate; and wherein the keratin hydrolysate is a hydrolysate of poultry feathers selected from the group consisting of chicken feathers, turkey feathers, duck feathers, and mixtures thereof.

3. The keratin hydrolysate as claimed in claim 1, wherein the content of each free amino acid, based on the total weight of the amino acids of the hydrolysate, is:
aspartic acid of 6.7%;
threonine of: 4.5%;
serine of: 10.9%;
glutamic acid of: 10.0%;
glycine of: 7.6%;
alanine of: 4.5%;
valine of: 7.2%;
methionine of: 0.2%;
isoleucine of: 4.0%;
leucine of: 6.7%;
phenylalanine of: 2.2%;
lysine of: 1.7%;
histidine of: 0.6%;
arginine of: 5.6%;
proline of: 10.3%;
tryptophan of: less than 0.1%;
L-cystine of: 5.0%;
cysteine of: less than or equal to 0.1%; and
tyrosine of: 0.2% by weight.

4. The hydrolysate as claimed in claim 1, wherein said hydrolysate has a true digestibility of the amino acids of at least 90%.

5. A dietary supplement comprising the keratin hydrolysate as claimed in claim 1, said dietary supplement comprising from 40% to 60% by weight of keratin hydrolysate relative to the total weight of said dietary supplement.

6. The dietary supplement as claimed in claim 5, wherein, with the exception of L-cystine, said dietary supplement comprises no free amino acids other than those contained in the hydrolysate.

7. The dietary supplement as claimed in claim 5, further comprising at least one component selected from the group consisting of zinc or a salt thereof, copper or a salt thereof, one or more B vitamins, and mixtures thereof.

8. The dietary supplement as claimed in claim 5, comprising:
said keratin hydrolysate in a content ranging from 0.001 to 2 g;
vitamin B3 in a content corresponding to 1% to 3% by weight of nicotinamide relative to the weight of the hydrolysate;
vitamin B5 in a content corresponding to 1% to 2% by weight of calcium pantothenate relative to the weight of the hydrolysate;
vitamin B6 in a content corresponding to 0.1% to 0.5% by weight of pyridoxine hydrochloride relative to the weight of the hydrolysate;
vitamin B8 in a content ranging from 0.01% to 0.1% relative to the weight of the hydrolysate;
zinc or a salt thereof in a content ranging from 0.5% to 2% of zinc relative to the weight of the hydrolysate; and
copper or a salt thereof in a content ranging from 0.05% to 0.5% of copper relative to the weight of the hydrolysate.

9. The dietary supplement as claimed in claim 5, wherein the dietary supplement comprises, besides the L-cystine contained in the keratin hydrolysate, an additional amount of L-cystine.

10. A method for preparing the keratin hydrolysate as claimed in claim 1 from poultry feathers, comprising at least the following steps, in this order:
subjecting the poultry feathers to at least one chemical hydrolysis by means of an acid under conditions suitable for obtaining a hydrolysate comprising from 88% to 95% by weight of free amino acids relative to the total weight of the amino acids of the hydrolysate, the remainder of the amino acids of the hydrolysate being in the form of peptides having a molecular mass less than or equal to 800 Dalton, the peptides being from 5% to 12% by weight relative to the total weight of hydrolysate;
extracting the tyrosine from said hydrolysate; and
optionally drying,
wherein the at least one chemical hydrolysis is carried out in two steps:
a first chemical hydrolysis carried out at a temperature ranging from 60° C. to 80° C. for a period ranging from 4 to 5 hours, then
a second chemical hydrolysis carried out at a temperature ranging from 100° C. to 115° C. for a period ranging from 5 to 7 hours, and
wherein the two hydrolyses may be carried out without an intermediate waiting step or by staging an intermediate waiting step of between 1 hour and 7 days.

11. A cosmetic treatment method for improving anchoring, gloss and/or volume and/or density of hair of an individual in need thereof, comprising orally administering to the individual an effective amount of the keratin hydrolysate as claimed in claim 1.

12. A cosmetic treatment method for improving quality and/or appearance of nails and/or of hair of an individual in need thereof, comprising orally administering to said individual an effective amount of the dietary supplement as claimed claim 5.

13. The method as claimed in claim 12, wherein the effective amount is a daily dose administered to an individual comprising:
a keratin hydrolysate in a content ranging from 0.001 to 2 g;
vitamin B3 in a content corresponding to a content ranging from 0.015 to 0.020 g of nicotinamide;
vitamin B5 in a content corresponding to a content ranging from 0.010 to 0.015 g of calcium pantothenate;
vitamin B6 in a content corresponding to a content ranging from 0.0004 to 0.0006 g of pyridoxine hydrochloride;
vitamin B8 in a content ranging from 0.0004 to 0.0006 g;
zinc or a salt thereof in a zinc content ranging from 0.008 to 0.0012 g; and
copper or a salt thereof in a copper content ranging from 0.001 to 0.002 g.

14. The method as claimed in claim 13, wherein the daily dose further comprises additional L-cystine in an amount by weight equal to the amount by weight of the hydrolysate.

15. A cosmetic treatment method for improving quality and/or appearance of nails and/or of hair of an individual in need thereof, comprising orally administering to said individual an effective amount of the keratin hydrolysate as claimed claim 1.

16. The method as claimed in claim 15, wherein the effective amount of said keratin hydrolysate is part of a daily dose administered to an individual comprising:
- said keratin hydrolysate in a content ranging from 0.001 to 2 g;
- vitamin B3 in a content corresponding to a content ranging from 0.015 to 0.020 g of nicotinamide;
- vitamin B5 in a content corresponding to a content ranging from 0.010 to 0.015 g of calcium pantothenate;
- vitamin B6 in a content corresponding to a content ranging from 0.0004 to 0.0006 g of pyridoxine hydrochloride;
- vitamin B8 in a content ranging from 0.0004 to 0.0006 g;
- zinc or a salt thereof in a zinc content ranging from 0.008 to 0.0012 g; and
- copper or a salt thereof in a copper content ranging from 0.001 to 0.002 g.

17. The method as claimed in claim 16, wherein the daily dose further comprises additional L-cystine in an amount by weight equal to the amount by weight of the hydrolysate.

\* \* \* \* \*